United States Patent [19]
Gonzalez

[11] Patent Number: 5,497,601
[45] Date of Patent: Mar. 12, 1996

[54] PACKAGING HAVING DISCRETE RETAINERS FOR A MEDICAL CATHETER AND METHOD

[75] Inventor: Rolando J. Gonzalez, Cooper City, Fla.

[73] Assignee: Cordis Corporation, Miami, Fla.

[21] Appl. No.: 292,910

[22] Filed: Aug. 19, 1994

[51] Int. Cl.⁶ .................................................. B65B 11/58
[52] U.S. Cl. ........................ 53/449; 53/450; 206/364
[58] Field of Search ................ 53/410, 449, 450, 53/456, 461, 416, 474; 206/363, 364, 461, 466

[56] References Cited

U.S. PATENT DOCUMENTS

| | | |
|---|---|---|
| 2,947,415 | 8/1960 | Garth . |
| 3,696,580 | 10/1972 | Saltzer, Sr. ............................... 53/449 |
| 3,850,084 | 11/1974 | Fowler et al. ............................ 53/449 |
| 3,851,649 | 12/1974 | Villari . |
| 3,967,728 | 7/1976 | Gordon et al. . |
| 4,467,588 | 8/1984 | Carveth ..................................... 53/449 |
| 4,779,727 | 10/1988 | Taterka et al. . |
| 4,850,526 | 7/1989 | Naef et al. ................................ 53/450 |
| 4,923,061 | 5/1990 | Trombley . |
| 5,131,537 | 7/1992 | Gonzalez . |
| 5,165,540 | 11/1992 | Forney ..................................... 206/364 |
| 5,353,929 | 10/1994 | Foster ...................................... 206/364 |

Primary Examiner—W. Donald Bray
Attorney, Agent, or Firm—Michael W. Montgomery

[57] ABSTRACT

Packaging for a medical catheter has a mounting card on which the catheter is placed and a cover sheet for covering the catheter to form a pouch or envelope. Discrete portions of the cover sheet are affixed to the mounting card on opposing sides of the catheter body, to restrict movement of the catheter from a desired shape.

17 Claims, 2 Drawing Sheets

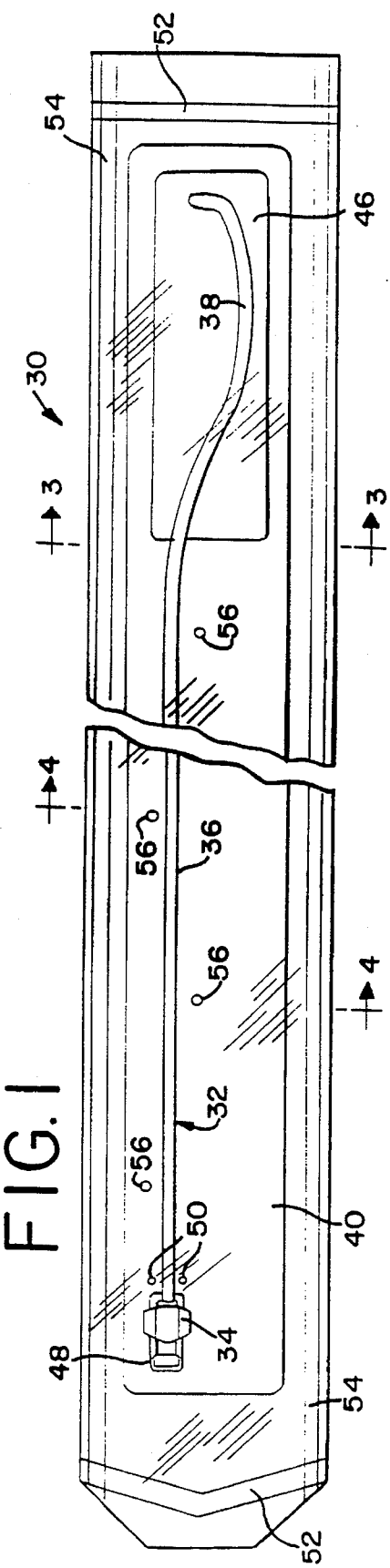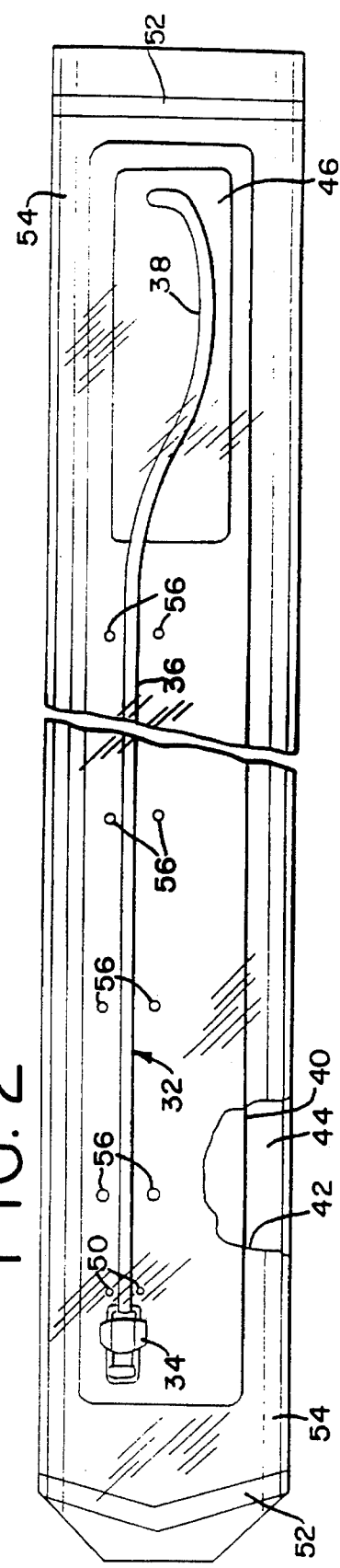

PACKAGING HAVING DISCRETE RETAINERS FOR A MEDICAL CATHETER AND METHOD

BACKGROUND AND DESCRIPTION OF THE INVENTION

The present invention generally relates to packaging for medical devices, and more particularly to packaging which includes a plurality of discrete retainers for restricting movement of a medical catheter from a desired shape.

Medical catheters of different types are used for a wide variety of purposes and techniques, including electrophysiology, neuroradiology, and coronary angioplasty and angiography. Coronary catheterization is conducted by inserting the tip of a catheter into an incision in the leg or arm of the patient, and then pushing the catheter into and through body passageways such as the lumen of a blood vessel, artery or heart passageway. The desired procedure is then performed at the distal tip of the catheter, such as injecting a radiopaque dye during angiography.

Coronary catheters generally have a proximal hub, a body, and a distal tip portion. The body and tip portion are formed of a long, flexible, tubular material having sufficient length to traverse a path from the incision to the coronary region. The body portion is relatively long and straight, while the tip portion is comparatively short and usually curved. The hub surrounds the proximal end of the catheter, and it has an axial passage and a coupling collar for connecting the catheter with a pressure source or dye reservoir. The hub may also have radially extending wings for enabling a physician to twist the hub and impart torque on the catheter to manipulate the distal tip portion.

The operational requirements of the catheter mandate the selection of a material having adequate characteristics, including flexibility, torque transmission, pushability, and resiliency. Flexibility enables the tubing of the catheter to wind its way through convoluted body passageways, such as through branching blood vessels and curved pathways within and into blood vessels, body cavities, or organs. The catheter should also adequately transfer torque so that the physician can manipulate and steer the distal tip portion by twisting the proximal hub. The catheter must possess sufficient longitudinal or column resistance, referred to as pushability, to negotiate through these passageways. Finally, the catheter must be resilient, tending to recover its prior shape after bending, referred to as shape memory. This being the case, catheters are often made of certain polyurethane materials that are advantageous for many uses, including coronary angiography and angioplasty applications.

Surgeons and medical teams request catheter tip portions having specially designed shapes, so that the catheter can be steered through the correct body passageways, and can perform the desired operation. It is thus important that these shapes be maintained accurately during manufacturing, sterilization, transport, storage, removal and utilization. The curved tip configuration must be maintained, not only during transport and storage, but also when the medical team slides the catheter and its curved tip from the packaging Just prior to a medical procedure. As a result, the packaging must not only protect the catheter, it must also maintain the desired shape of the catheter until the catheter is used.

Accordingly, it is desirable to retain the body of the catheter in as straight a position as possible so that it does not induce any trauma to the body and retains acceptable pushability. However, the tip portion is intentionally curved and must recover to this desired shape after the catheter is removed from the packaging. The catheter is conventionally removed from the packaging by partially peeling the upper web from the lower web in the area near the proximal hub of the catheter, and then longitudinally pulling the catheter from the packaging by grasping the hub. As the catheter is removed, the curved tip portion directly contacts each of the cross-foot serrations sequentially. The packaging should therefore preferably minimize any bending stress on the curved tip portion during placement into, storage within, and removal from the packaging.

An example of previous packaging for a catheter is described in U.S. Pat. No. 5,131,537, filed on Oct. 3, 1991, which is entitled "Flexible Tip Tray Packaging for Medical Catheters", which is commonly assigned and includes a relatively stiff mounting card, an upper web, a lower web, and a flexible tip tray. The upper web has been formed of extruded Mylar® material, while the lower web has been made of porous Tyvek® material. The upper and lower webs are peripherally sealed to define a pouch containing the mounting card and catheter. The tip tray is provided for protecting and maintaining the desired curve of the distal tip portion of the catheter during storage. The mounting card has a hub recess hole for partially receiving the hub of the catheter, to reduce damage by the hub to the upper web.

The catheter body portion was retained in a straight position relative to the mounting card by a plurality of cross-foot serrations which contact the catheter body directly. While the cross-foot retainers perform their intended function adequately, it is desirable to provide retainers which restrict movement of the catheter body from a straight position, yet which do not directly contact the catheter or require the card to be cut. In addition, the catheter must presently be placed into the cross-foot serrations manually, so it would be advantageous to provide packaging having a design which can be assembled in an automated process.

It is accordingly a general object of the present invention to provide an improved catheter packaging assembly which restricts movement of the catheter from a desired position without directly contacting the catheter body, and which can be manufactured in an automated process.

An additional object of the present invention is to provide improved retainers for use in packaging for a medical catheter which do not require a mounting card to be perforated.

The unique packaging assembly of the present invention incorporates a plurality of discrete retainer elements which do not directly contact the catheter body, yet restrict its movement from a desired position. The retainer elements of the present invention are preferably formed by simultaneously applying heat and pressure to the cover sheet to partially melt it, thus Joining a portion of the cover sheet to the mounting card without requiring serrations. Moreover, the packaging of the present invention may be assembled by an automated process.

These and various other objects, advantages and features of the invention will become apparent from the following description and claims, when considered in conjunction with the appended drawings.

BRIEF DESCRIPTION OF THE DRAWINGS

FIG. 1 is a top plan view of packaging for a medical catheter, according to the principles of the present invention;

FIG. 2 is a top plan view of packaging for a medical catheter, according to an alternative embodiment of the present invention;

DETAILED DESCRIPTION OF THE PREFERRED EMBODIMENTS

Figure 3:
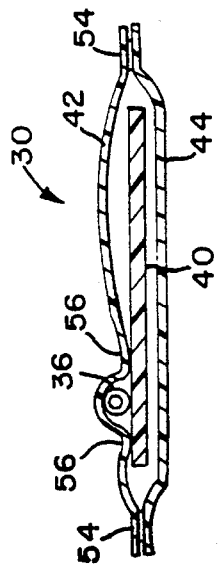
FIG. 3 is a cross-sectional view of the packaging of the present invention, along the lines 3—3 in FIG. 1.

The following description of the preferred embodiments of the present invention is merely illustrative in nature, and as such it does not limit in any way the present invention, its application or uses. Numerous modifications may made by those skilled in the art without departing from the true spirit and scope of the invention.

With reference to the drawings, the packaging assembly of the present invention is generally designated by reference numeral 30. Packaging assembly 30 encloses and protects a medical catheter, such as the representative right ventricular angiography catheter 32 shown in FIGS. 1 and 2. The packaging assembly 30 of the present invention may of course be used with any of various different types of medical catheters. Catheter 32 is generally a long, thin, flexible tube formed of a polyurethane or nylon material, to which a rigid hub 34 is affixed at a proximal end. A long, straight body portion 36 extends from hub 34 to a resilient curved tip portion 38, which may have a variety of desired shapes for given purposes.

The packaging assembly 30 generally includes a mounting card 40, an upper and lower outer sheet 42 and 44, and a flexible tip tray 46 for releasably enclosing and protecting curved tip portion 38. The mounting card 40 may be made of either high density polyethylene (HDPE) having a thickness of approximately 0.015 to 0.020 inches, or a claycoated, solid bleached sulphate (SBS) board having a thickness of approximately 0.006 to 0.012 inches. Upper sheet 42 should preferably be made of Mylar® material, while lower sheet 44 is preferably porous Tyvek® material. Mylar® material has two co-extruded components, a polyethylene and a polyester. At a temperature of approximately 345° F., the polyethylene component of the material will melt, whereas the polyester component of the material will remain in the solid phase. The term "melt" as used herein includes the melting of a single component of a compound material.

The tip tray 46 is described in greater detail in the commonly assigned U.S. Pat. No. 5,131,537, filed on Oct. 3, 1991, entitled "Flexible Tip Tray Packaging for Medical Catheters", the disclosure of which is incorporated herein by reference. The tip tray 46 releasably encloses the tip portion 38 of the catheter 32, and rests upon mounting card 40. Mounting card 40 has no openings or perforations other than a hub recess opening 48 for partially receiving hub 34, and an optional pair of alignment holes or alignment openings 50. As such, mounting card 40 has no perforation in close proximity to the catheter body 36.

Hub recess opening 48 reduces the possibility of damage to the upper outer sheet 42 caused by contact between the hub 34 and the outer sheet 42. If desired, alignment openings 50 may be provided in mounting card 40 to facilitate the assembly of packaging 30 by an automated process.

Upper and lower outer sheets 42 and 44 are sealed together by the simultaneous application of heat and pressure, to form overlapping end seals 52 and longitudinal edge seals 54. Seals 52 and 54 thus join sheets 42 and 44 along their respective perimeters, creating a sealed envelope for containing and protecting the catheter 32, mounting card 40, and tip tray 46. The resulting sealed envelope is sterilized and stored until the catheter 32 is to be used.

Figure 4:
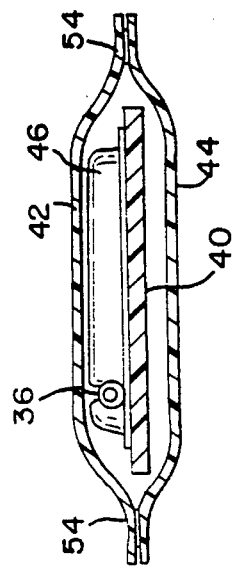
FIG. 4 is a cross-sectional view of the packaging of the present invention, along the lines 4—4 in FIG. 1.

The unique configuration of the present invention provides a novel arrangement of discrete retainer elements which tend to restrict movement of catheter body 36 from the desired straight position illustrated in FIGS. 1 and 2, yet without directly contacting the catheter body 36. A preferred embodiment of the retainer elements of the present invention is illustrated in FIGS. 1 and 4, in which several retainers 56 are each defined by a local area where the upper cover sheet 42 is fastened to the mounting card 40.

The retainers 56 are preferably formed by simultaneously applying heat and pressure to the upper outer sheet or cover sheet 42 to partially melt it, thus joining a portion of the upper outer sheet 42 to the mounting card 40. In the alternative, retainers 56 may also be formed by utilizing separate fastening members to affix portions of the upper sheet 42 to the mounting card 40, or by applying a polyethylene coating onto mounting card 40 before upper sheet 42 is applied. Regardless of the method by which the retainers 56 are made, it is important that the process does not puncture or tear upper sheet 42 so that the catheter 32 can be maintained in a sterile environment.

Retainers 56 are preferably arranged in the alternating pattern shown in FIG. 1, in which one retainer 56 is disposed on the mounting card 40 on one side of the catheter body 36, while the next longitudinally successive retainer 56 is located on the opposite side of the catheter body 36. In the alternative, retainers 56 may be arranged in opposing pairs on opposite sides of the catheter body 36, as depicted in FIG. 2.

Retainer elements 56 are laterally spaced slightly away from the desired straight position of catheter body 36, to reduce the possibility of a retainer being formed in contact with catheter body 36 due to misalignment. Further, retainers 56 are preferably spaced apart longitudinally along the length of the catheter body 36, to reduce bending stress imposed on the curved tip portion 38 as the catheter 32 is removed from the packaging 30 by sliding it longitudinally outward.

Likewise, the quantity of retainers 56 should be carefully selected. The number of retainers 56 should be as few as possible to minimize stress to the curved tip portion 38 as the catheter 32 is removed from the packaging 30, and also to enable the resilient tip portion 38 to recover its shape during and after removal. On the other hand, packaging 30 should include a sufficient number of retainers 56 to effectively retain the position of the catheter body 36 without large deviations from the desired straight position. It has been discovered that an acceptable number of retainers 56 for an angiographic catheter having a length of approximately 100 centimeters is approximately five to ten.

The retainers 56 of the present invention thus retain the catheter body 36 in a generally straight position without directly contacting the catheter 32. The catheter body 36 only touches an upper surface of the mounting card 40 and an inner surface of cover sheet 42. Retainers 56 thus facilitate easy removal of the catheter 32 from packaging 30 and enhance sterilization.

Figure 5:
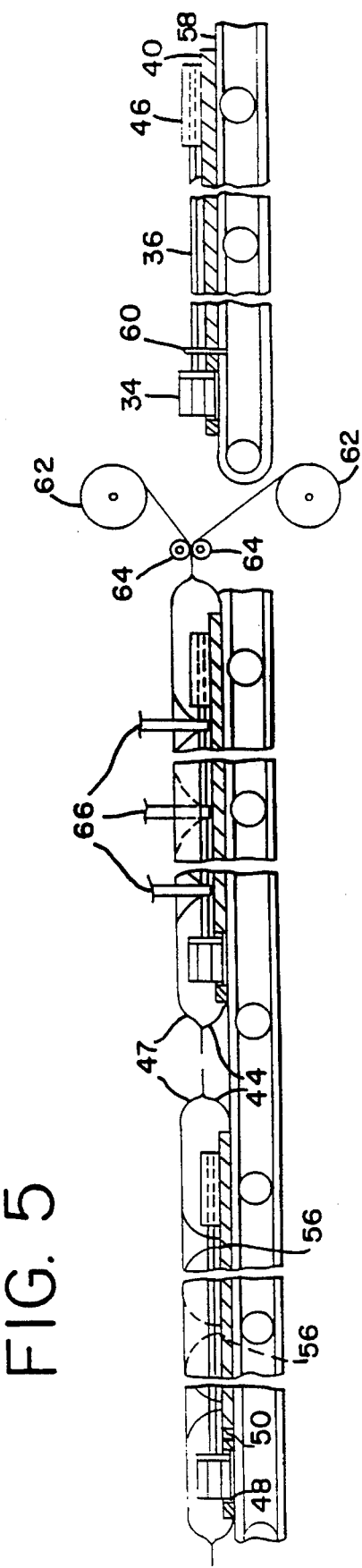
FIG. 5 is a diagrammatic representation of a method of assembling packaging for a medical catheter, according to the principles of the present invention.

The method of assembling packaging 10 is illustrated in FIG. 5. First, the tip portion 38 of the catheter 32 is inserted within tip tray 46. The catheter 32 and tip tray 46 are then placed on mounting card 40, which preferably is placed on a moving operating surface or conveyor 58. Hub 34 is placed within hub recess opening 48 as shown in FIGS. 1, 2 and 5. Mounting card 40 may be aligned on conveyor 58 by inserting a pair of aligning pins 60 into aligning holes 50. A proximal portion of the catheter body 36 is thus aligned between aligning pins 60 and alignment holes 50. Mounting card 40 and catheter 32 are then moved on conveyor 58 into a wrapping area, while an aligning fork (not shown) is dragged along the catheter body 36 to align it in the desired straight position on mounting card 40 depicted in FIGS. 1 and 2. Upper and lower outer sheets 42 and 44 are dispensed from rolls 62 and simultaneously applied to mounting card 40 and catheter 32. End seals 52 and edge seals 54 are formed, for example by heated rollers 64, to partially melt upper sheet 42 and Join it with lower sheet 44, defining the desired sealed envelope. The retainers 56 of the present invention are then formed by utilizing heated dies 66 to simultaneously apply localized heat and pressure to partially melt the cover sheet 42 and fasten it to the mounting card 40. It is believed that dies 66 should be heated to a temperature approximately within the range of 300°–400° F., and should preferably define a heating surface which is preferably a circle having a diameter of approximately ¼ inch or less.

If a solid bleached sulphate (SBS) board is selected for mounting card 40, then the retainers 56 should preferably have a diameter of approximately ¼ or ⅓ inch. Retainers 56 may be spaced longitudinally along the SBS mounting card 40 by a distance of approximately three to six inches, while they should be laterally spaced by a span of approximately ¾ inch between centers of the retainers 56. Heated dies 66 should be pressed onto packaging 30 towards operating surface 58 with relatively light pressure for a time period of approximately two to ten seconds. It is believed that heated dies 66 should impose a force of approximately five pounds or less, causing a pressure approximately within the range of 40–60 pounds per square inch. The upper sheet 42 will partially melt and adhere to mounting card 40, yet the SBS mounting card 40 may not melt. Upper sheet 42 can then be peeled back from a mounting card 40 to remove catheter 32 from packaging 30, and the melted portions of upper sheet 42 which define retainers 56 will also peel away from the SBS mounting card 40.

On the other hand, if high density polyethylene (HDPE) is selected for mounting card 40, then retainers 56 may have a diameter as small as approximately 1/16 or 1/10 inch, and may be formed in a time period as short as a fraction of a second. In this case, the polyethylene component of upper sheet 42 and the polyethylene mounting card 40 will both melt to form retainers 56. When the upper sheet 42 is removed, it will rip in the local areas of the retainers 56, because the portions of upper sheet 42 which define retainers 56 will have melted into and mixed with corresponding melted portions of mounting card 40. Because retainers 56 formed with a polyethylene mounting card 40 can be so small, they are not obviously apparent and thus provide an aesthetically pleasing way to hold the catheter body 36 in the desired straight position.

The method of the present invention thus enables the catheter body 36 to be aligned and retained in the desired position with respect to the mounting card 40 in an automated process, without requiring the catheter 32 to be inserted within fastening members manually. The resulting retainers 56 also have the advantage feature of resisting gross deviation of the catheter body 36 from the desired straight position, yet without directly contacting the catheter 32.

It should be understood that an unlimited number of configurations for the present invention can be realized. The foregoing discussion describes merely exemplary embodiments of the principles of the present invention. Those skilled in the art will readily recognize from the description, claims, and drawings that numerous changes and modifications can be made without departing from the spirit and scope of the invention.

I claim:

1. Packaging for a medical catheter, comprising:
    a mounting card on which a medical catheter is disposed;
    a cover sheet which forms a sealed envelope enclosing said medical catheter; and
    a plurality of discrete retainers, each retainer being defined by a portion of said cover sheet which is fastened to said mounting card, for restricting movement of said catheter from a desired shape.

2. Packaging for a medical catheter, comprising:
    a mounting card on which a medical catheter is disposed;
    a first and second outer sheet which are sealed together along their respective perimeters to form an envelope enclosing said mounting card and catheter; and
    a plurality of discrete retainers, each retainer being defined by a portion of said cover sheet which is fastened to said mounting card, for restricting movement of said catheter from a desired shape.

3. The packaging for a medical catheter as set forth in claim 2, wherein said retainers are formed by a melted portion of said first outer sheet which is affixed to said mounting card.

4. The packaging for a medical catheter as set forth in claim 2, wherein said retainers are laterally spaced apart, out of direct contact with said catheter.

5. The packaging for a medical catheter as set forth in claim 2, wherein said catheter is directly contacted only by said first outer sheet and a first surface of said mounting card.

6. The packaging for a medical catheter as set forth in claim 2, wherein a distal tip portion of said medical catheter is formed in a preselected curved shape, said retainers being disposed along a relatively straight body portion of said medical catheter, said retainers being longitudinally spaced apart from each other, such that said retainers impose reduced bending stress on said tip portion of said medical catheter when said medical catheter is longitudinally pulled from said packaging.

7. The packaging for a medical catheter as set forth in claim 2, wherein said retainers are disposed in relation to said mounting card in opposing pairs on opposite sides of said catheter body.

8. The packaging for a medical catheter as set forth in claim 2, wherein one of said outer sheets is formed of a porous material.

9. The packaging for a medical catheter as set forth in claim 2, further comprising a flexible tip tray disposed within said envelope and having a flexible groove for receiving and releasably securing a curved tip portion of said medical catheter, for protecting said curved tip portion and for maintaining said tip portion in a preselected curved shape, while allowing said catheter to be longitudinally pulled from said tip tray.

10. The packaging for a medical catheter as set forth in claim 2, wherein said mounting card further comprises a hub recess opening for partially receiving said hub.

11. The packaging for a medical catheter as set forth in claim 2, wherein said mounting card is formed without any perforation in proximity to said retainers.

12. The packaging for a medical catheter as set forth in claim 2, wherein said mounting card further comprises a pair of alignment openings for removably receiving an alignment member.

13. The packaging for a medical catheter as set forth in claim 2, further comprising a flexible tip tray having a flexible groove for receiving and releasably securing a curved tip portion of said medical catheter.

14. A method of assembling packaging for a medical catheter, comprising the steps of:

a) placing a catheter onto a mounting card;

b) applying a first and second outer sheet about said catheter and mounting card;

c) sealing said first and second outer sheet together along their respective perimeters, thereby forming an envelope which encloses said mounting card and catheter; and d) fastening discrete portions of said first outer sheet to said mounting card to form a plurality of retainer elements for restricting movement of the catheter from a desired shape.

15. The method of assembling packaging for a medical catheter as set forth in claim 14, in which said step (d) is performed by applying localized heat and pressure to said first outer sheet to partially melt a portion of said first outer sheet to form said retainer elements.

16. The method of assembling packaging for a medical catheter as set forth in claim 14, in which said step (a) further comprises the additional step of aligning said mounting card on an operating surface by inserting a pair of aligning pins through a corresponding pair of alignment holes formed in said mounting card, and aligning a portion of said catheter between said aligning pins.

17. The method of assembling packaging for a medical catheter as set forth in claim 16, further comprising the additional step immediately preceding said step b) of aligning said catheter in a desired position relative to said mounting card by dragging an alignment fork along a portion of said mounting card.

* * * * *